(12) United States Patent
Yamamoto et al.

(10) Patent No.: US 7,985,595 B2
(45) Date of Patent: Jul. 26, 2011

(54) METHOD FOR EXTRACTING A BIOSUBSTANCE FROM HAIR AND HAIR SAMPLING DEVICE USEFUL IN THE METHOD

(75) Inventors: Takuro Yamamoto, Kanagawa (JP); Tomoteru Abe, Kanagawa (JP); Kazuhiro Nakagawa, Saitama (JP); Shiko Yamashita, Tokyo (JP); Haruhiko Soma, Tokyo (JP); Noriyuki Kishii, Kanagawa (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 12/893,483

(22) Filed: Sep. 29, 2010

(65) Prior Publication Data

US 2011/0015651 A1    Jan. 20, 2011

Related U.S. Application Data

(62) Division of application No. 12/033,803, filed on Feb. 19, 2008.

(30) Foreign Application Priority Data

Mar. 1, 2007  (JP) ................ P2007-051449
Sep. 20, 2007 (JP) ................ P2007-243237

(51) Int. Cl.
*A61B 17/50* (2006.01)
*A61B 17/00* (2006.01)

(52) U.S. Cl. ............ 436/174; 606/133; 606/131; 606/1

(58) Field of Classification Search ................... 436/174; 606/133, 131, 1

See application file for complete search history.

(56) References Cited

U.S. PATENT DOCUMENTS

| 5,221,280 A | 6/1993 | Gross et al. |
| 5,885,766 A | 3/1999 | Mahe et al. |
| 6,399,057 B1 | 6/2002 | Gho |
| 6,478,750 B1 | 11/2002 | Morrison et al. |
| 6,544,259 B1 | 4/2003 | Tsaliovich |
| 2004/0247573 A1 | 12/2004 | Kim et al. |
| 2005/0201904 A1 | 9/2005 | Stripling et al. |

FOREIGN PATENT DOCUMENTS

| JP | 56-50809 | 11/1981 |
| JP | 04-94549 | 8/1992 |
| JP | 06-007326 | 1/1994 |
| JP | 2001-021815 | 1/2001 |
| JP | 2001-526560 | 12/2001 |
| JP | 2004-045133 | 2/2004 |
| JP | 2004-215967 | 8/2004 |
| JP | 2005-512642 | 5/2005 |
| JP | 2005-192409 | 7/2005 |
| JP | 2006-053101 | 2/2006 |
| WO | WO 2005/079687 | 9/2005 |

OTHER PUBLICATIONS

M.E. Roersma et al., "The Failure Behavior of the Anchorage of Hairs During Slow Extraction," Journal of Biomechanics, vol. 34, 2001, pp. 319-325.

Communication from Japanese Patent Office dated Dec. 24, 2008 for Japanese Patent Application No. 2007-243237, 5 pgs.

Alibardi Lorenzo, "Comparative Aspects of the Inner Root Sheath in Adult and Developing Hairs of Mammals in Relation to the Evolution of Hairs," J. Anat. 2004, 205, pp. 179-200.

*Primary Examiner* — Walter D Griffin
*Assistant Examiner* — Christine T Mui
(74) *Attorney, Agent, or Firm* — Finnegan, Henderson, Farabow, Garrett & Dunner, L.L.P.

(57) ABSTRACT

Disclosed herein is a method for extracting a biosubstance from a root of a hair, including the step of using as the hair a hair that has pulling force of at least a predetermined reference value to pull out the hair.

19 Claims, 15 Drawing Sheets

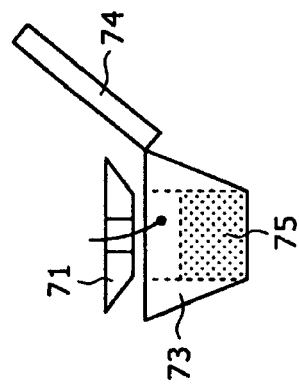
FIG.12C
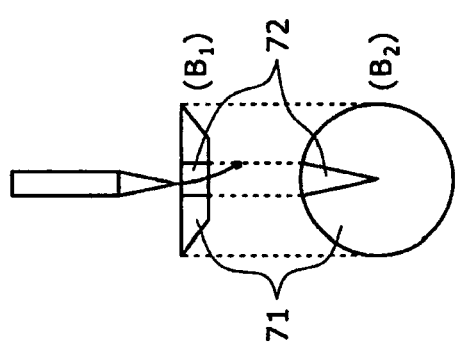
FIG.12B
FIG.12A
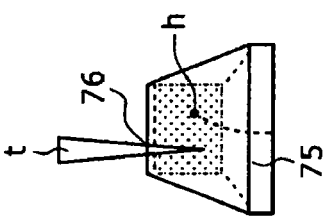
FIG.12F
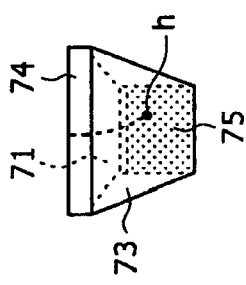
FIG.12E
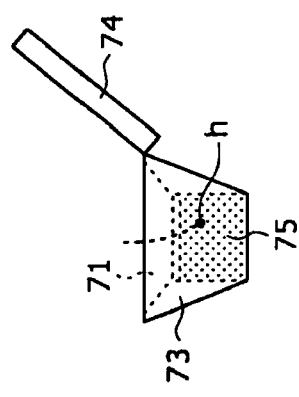
FIG.12D FIG.16A
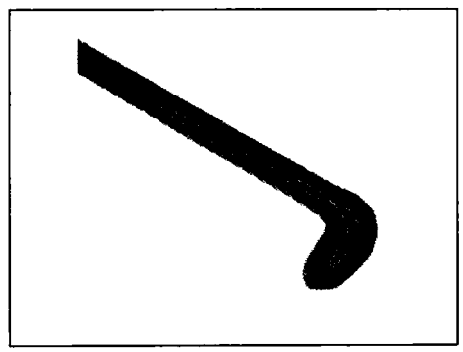
FIG.16B
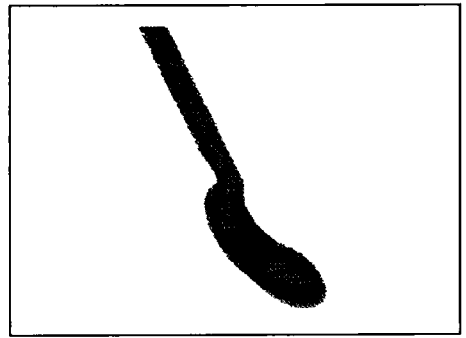
FIG.16C
|  | PULLING ANGLE NOT SPECIFIED | PULLING ANGLE SPECIFIED |
|---|---|---|
| QUANTITY OF EXTRACTED RNA (ng) | 40.14 | 93.93 |

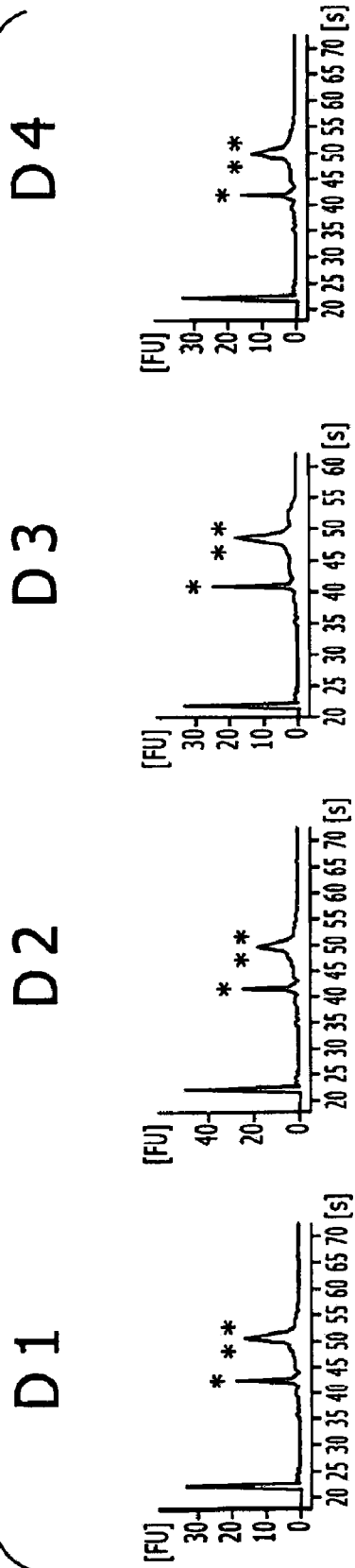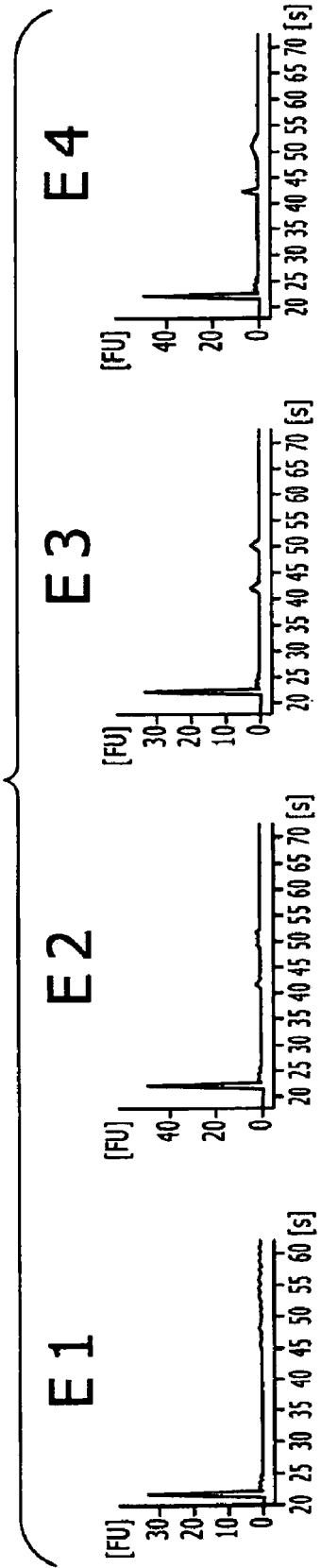
FIG. 18A
FIG. 18B

METHOD FOR EXTRACTING A BIOSUBSTANCE FROM HAIR AND HAIR SAMPLING DEVICE USEFUL IN THE METHOD

CROSS REFERENCES TO RELATED APPLICATIONS

This is a divisional of application Ser. No. 12/033,803, filed Feb. 19, 2008 and currently allowed. Application Ser. No. 12/033,803 claims priority to Japanese Patent Application JP 2007-051449, filed Mar. 1, 2007 and to Japanese Patent Application JP 2007-243237, filed Sep. 20, 2007. All of the applications are incorporated herein by reference in their entirety.

BACKGROUND OF THE INVENTION

1. Field of the Invention

This invention relates to a method for extracting a biosubstance from the root of a hair. More specifically, the present invention is concerned with a method for extracting a biosubstance such as RNA, DNA, protein or element from the root of a hair that requires pulling force of at least a predetermined reference value to pull it out and also with a hair sampling device useful in the method.

2. Description of the Related Art

These days, diverse gene expression analyses led by DNA microarrays are widely used to elucidate the molecular mechanisms of various diseases and also to search disease markers and drug targets.

For a DNA microarray, RNA is firstly extracted from a sample tissue or sample cells, and cDNA is then synthesized with a reverse transcriptase while using the RNA as a template. Upon this synthesis, the cDNA is labeled with a phosphor such as Cy3 or Cy5, followed by hybridization of the labeled cDNA with probe DNA immobilized on the microarray. Based on fluorescence signals from the hybridized cDNA, an expressed gene is analyzed.

DNA microarrays in the past have been considered to require RNA in a substantial quantity (on the order of several micrograms) for the provision of the above-described labeled cDNA. Accordingly, targets of analyses were limited to relatively large tissue fragments and large quantities of cells, and analyses of small tissue fragments and small quantities of cells such as biopsy samples were difficult.

In recent years, however, high-sensitivity DNA microarrays have been developed to permit measurements of nanogram-level gene samples, thereby making it possible to also perform gene expression analyses on micro-volume samples such as small tissue fragments and small quantities of cells. It has also become increasingly possible to perform micro-volume sample analyses in gene polymorphism analyses, proteome analyses and the like.

These micro-volume sample analyses have attracted increasing interests as permitting easy sample collections at actual clinical sites and also enabling to accumulate samples and their analysis data and also to establish fast diagnosis methods.

In a gene polymorphism analysis, for example, it has heretofore been necessary to sample blood as much as 10 mL or so to collect leucocytes from the blood, to lyse leucocytes to extract DNA, to amplify the DNA by a PCR, and then to perform a gene polymorphism analysis. At present, however, systems have been put on the market to perform the extraction of DNA from a micro-volume sample such as a drop of blood obtained by slightly puncturing a fingertip or an extremely small piece of mucosa collected by scratching off the tunica mucosa oris, its amplification and even the determination of its genotype in a fully automated fashion.

Keeping in step with the increasing practice of the analysis of biosubstances such as RNA, DNA, proteins and elements from such micro-volume samples, hair is attracting interests as samples in addition to the above-mentioned blood drops and tunica mucosa oris. Hair can be noninvasively and simply collected or sampled without imposing heavy physical or mental pain or suffering on donors (patients). Hair is, therefore, expected to serve as a suitable source for the extraction of biosubstances toward the popularization of order-made medical care such as the diagnosis of drug sensitivity by the single-base polymorphism (SNP) analysis of genes.

As a method for the diagnosis of a disturbance in physical conditions, a method to detect an element contained in a hair root has been developed (see Japanese Patent Laid-open No. 2004-45133 referred to as Patent Document 1 hereinafter).

Further, Japanese Patent Laid-open No. 2005-192409 (referred to as Patent Document 2 hereinafter) discloses, as a method for the recovery of RNA from hair such as head hair, a method that freezes up a hair to extreme cold with liquefied nitrogen immediately after its pull-out, brings the frozen hair into contact with an RNA extracting reagent, and then subjects the resulting hair to vortex agitation processing to extract RNA.

SUMMARY OF THE INVENTION

The above-described diagnosis method disclosed in Patent Document 1 makes it possible to perform an easy diagnosis of a disturbance in physical conditions by detecting an element contained in a hair root. The RNA extraction method disclosed in Patent Document 2, on the other hand, makes it possible to readily extract RNA from a hair in high yield with high purity.

However, no investigations have been made about appropriate conditions for hair to be employed for the extraction of biosubstances such as RNA, DNA, proteins or elements.

Hair is known to repeat a cycle called "hair cycle" which is composed of three phases, that is, the anagen phase, the catagen phase and the telogen phase. Depending on which phase a hair to be used is in, the conditions of its hair root differs significantly. Depending on the conditions of a hair root, variations hence arise in the quantity and quality of a biosubstance such as RNA, DNA, protein or element to be extracted from the hair root. These variations still remain as a factor that makes it difficult to assure the reproducibility of the results of an analysis making use of such a biosubstance.

Moreover, to avoid variations in the quantity and quality of a biosubstance, an unnecessarily large number of hairs may be taken out upon collecting or sampling hair, or hair has to be collected or sampled again from the donor (patient). This is inefficient and also gives inconvenience and suffering to the donor.

Purposes of the present invention are, therefore, to provide a method for extracting a biosubstance such as RNA, DNA, protein or element from a pulled-out hair stably in both quantity and quality and a hair sampling device useful in the method.

To achieve the above-described purposes, the present invention provides a method for extracting a biosubstance, such as RNA, DNA, protein or element, from a root of a hair, including using as the hair a hair that has pulling force of at least a predetermined reference value to pull out the hair. As the reference value, 50 g is preferred. The present invention also provides a hair sampling device for pulling out a hair, including means for holding the hair, and means for measuring pulling force applied to the hair upon pulling out the hair.

The hair sampling device may further include means for specifying a pull-out direction of the hair relative to a body surface or means for enabling magnifying observation of a shape of a root of the pulled-out hair.

The hair sampling device may further include means for acquiring hair-root image information on the pulled-out hair and means for determining a shape of a root of the pulled-out hair on a basis of the hair-root image information acquired by the acquisition means.

The hair sampling device may further include storage means for storing reference hair-root image information acquired beforehand, wherein the determination means determines the shape of the hair root on a basis of a comparison between the hair-root image information acquired by the acquisition means and the reference hair-root image information.

In the hair sampling device described in the immediately preceding paragraph, the determination means may perform the comparison by detecting inflection points on a contour of the hair root and counting the inflection points.

In the present invention, the term "hair" means all hair that covers the skin (body surface) of a human or non-human animal. Taking a human as an example, the term "hair" embraces hair on the head, hair on the face, hair on the arms and legs, and the like. The term "(hair) root" as used herein, on the other hand, means an end portion of each hair on a side lying under the body surface. The root of a pulled-out hair can be accompanied by an island that forms an inner root sheath, an outer root sheath, a papilla and the like.

Use of the biosubstance extraction method according to the present embodiment makes it possible to extract a biosubstance such as RNA, DNA, protein or element from a hair stably in both quantity and quality. The hair sampling device according to the present embodiment can be suitably used for the extraction method.

BRIEF DESCRIPTION OF THE DRAWINGS

FIGS. 12A through 12F are schematic illustrations of a kit in different stages of use for extracting a biosubstance from a pulled-out hair;

FIG. 16A shows an enlarged image of the root of a hair pulled out without allowing the angle of its growing direction to change relative to the body surface, FIG. 16B depicts an enlarged image of the root of a hair pulled out at a non-specified angle, and FIG. 16C is a table presenting concentrations of RNA solutions extracted from those hair roots, respectively;

FIGS. 18A and 18B (D1 through E4) diagrammatically illustrate electrophoresis patterns of RNAs obtained from the hair roots in Groups D and E of FIG. 17, respectively.

DETAILED DESCRIPTION OF THE PREFERRED EMBODIMENTS

As mentioned above, the quantity and quality of a biosubstance such as RNA, DNA, protein or element extracted from the root of a hair considerably differ depending on which one of the hair cycle of the anagen, catagen and telogen phases the hair is in.

Figure 1:
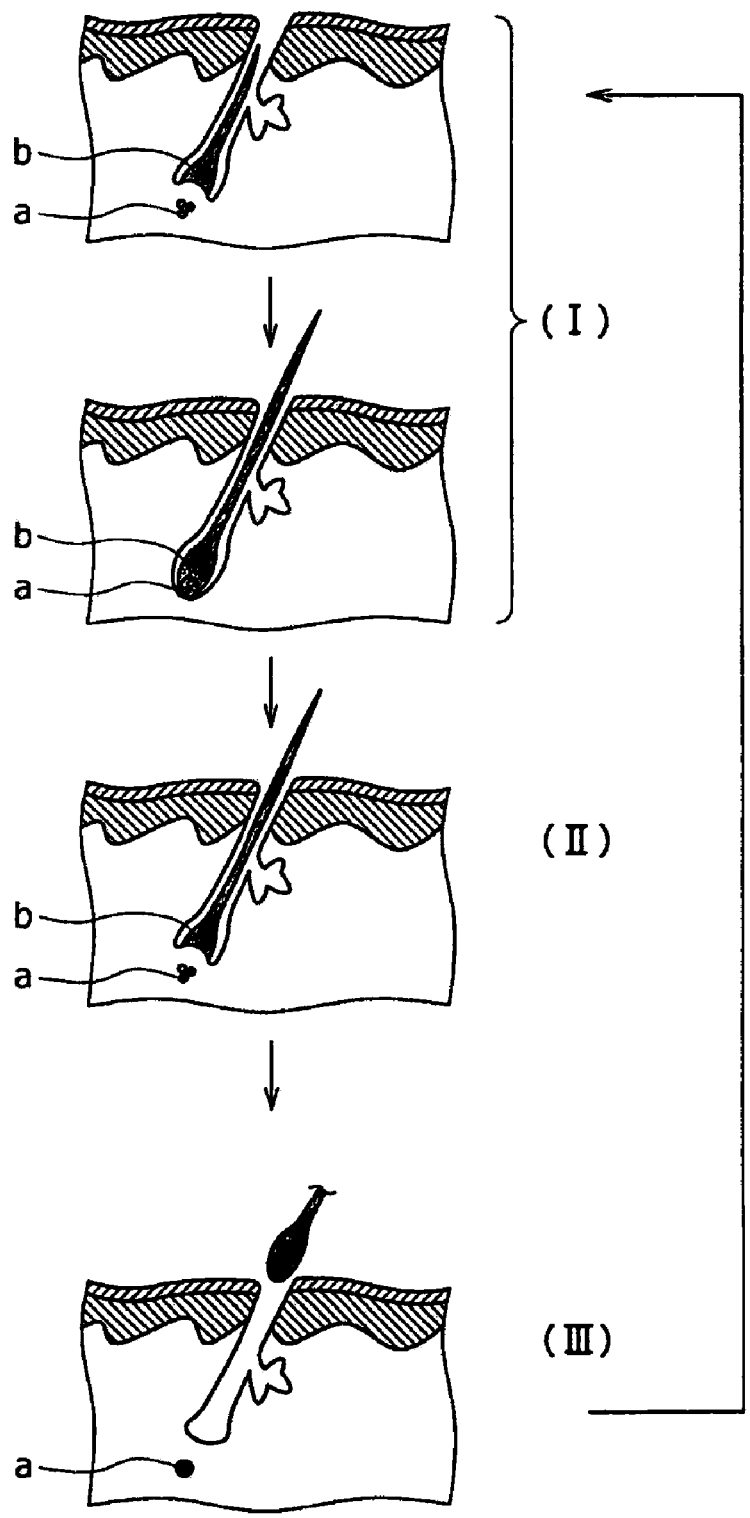
FIG. 1 shows schematic diagrams of a skin cross-section to describe the hair cycle.

With reference to FIG. 1, a description will now be made about the structure of a hair and the hair cycle.

FIG. 1 shows schematic diagrams of a skin cross-section. A hair is formed of a hair shaft exposed to the outside of the skin, a hair root lying in the dermis, and papilla cells (reference sign a in FIG. 1) and hair matrix cells (reference sign b in FIG. 1) both of which act as sources for creating the hair root.

The hair cycle is divided into three phases including the anagen phase (I), the catagen phase (II) and the telogen phase (III). In the anagen phase (I), nutrition is supplied from the papilla cells a to the hair matrix cells b so that the hair matrix cells b actively divide. The divided hair matrix cells b turn into hair cells and keratinize, and by hair cells formed successively, are pushed upward to form a hair.

When the hair cycle subsequently enters the catagen phase (II), the hair matrix cells b terminate division. When the hair cycle advances further to enter the telogen phase (III), the supply of nutrition from the papilla cells a to the hair matrix cells b stops, the hair matrix cells b die by apoptosis, and eventually, the hair falls off. After a certain period of the telogen phase (III), the hair cycle again enters the anagen phase (I).

As described above, it is in the anagen phase (I) of the hair cycle that cell division is most active at a hair root and the number of cells existing at the cell root becomes greatest. Upon conducting extraction of a biosubstance from a hair root, it is hence desired to conduct the extraction from a hair in the anagen phase (I) so that the biosubstance can be extracted substantially in both quantity and quality.

If the extraction of the biosubstance is conducted from the root of a hair in the catagen phase (II) or the telogen phase (III), the cells of the hair root in this phase are in a state that their division is halted, and in the case of RNA, for example, are in a state that the transcription activity in the cells is extremely low so that RNA may not be extracted in any sufficient quantity.

Figure 2:
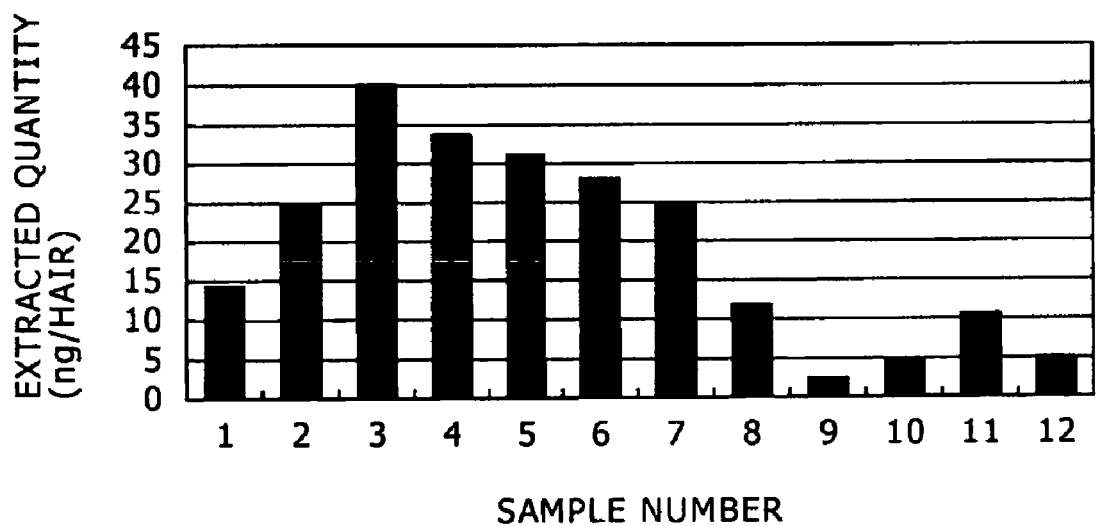
FIG. 2 is a diagram illustrating quantities of RNA extracted from hairs pulled out at random.

FIG. 2 illustrates quantities of RNA extracted from the roots of respective hairs when the hairs were pulled out at random. In FIG. 2, the abscissa represents the sample numbers of respective hairs, while the ordinate represents the concentrations (ng/hair) of RNA solutions prepared from the respective samples. An extraction method of RNA in the present invention will be described subsequently herein in detail.

The concentrations of the RNA solutions prepared from the hairs of the sample numbers 1 to 12, respectively, significantly vary from several ng/hair to 40 ng/hair. It is, therefore, appreciated that RNA may not be extracted in any stable quantity from hairs pulled out at random.

The present inventors conducted an extensive investigation to eliminate such variations. As a result, it has been found that a biosubstance can be obtained stably in both quantity and quality by choosing the root of a hair that has pulling force of at least a predetermined reference value to pull it out and then conducting the extraction of the biosubstance.

As mentioned above, in the catagen phase (II) or the telogen phase (III), the hair matrix cells b stop division and die by apoptosis so that the hair is in the state that it very easily falls off. In the anagen phase (I), in contrast, the hair matrix cells b actively divide so that the hair root is in a state filled with cells so that the hair hardly falls off. A hair in the anagen phase (I), therefore, requires greater pulling force upon pulling it out than a hair in the catagen phase (II) or the telogen phase (III). In other words, hairs that have pulling force of at least a predetermined reference value to pull them out can be considered to be hairs in the anagen phase (I) so that the selection of such hairs is believed to permit obtaining a biosubstance stably in both quantity and quality.

This method can be applied to all hair that covers the skin of a human or non-human animal, and in particular, can be suitably applied to human hair. It is possible to more surely obtain a hair in the anagen phase (I) by once shaving off hair in its entirety at a sampling position and choosing a newly-grown hair.

The predetermined reference value that makes it possible to distinguish a hair in the anagen phase (I) from those in the catagen phase (II) or the telogen phase (III) can be set suitably depending on the animal species or the position of hair to which the present invention is applied. It has been found that, when the method of the present invention is applied to human hair, a biosubstance to be extracted can be optimized in both quantity and quality by setting the reference value at 50 g.

It is to be noted that setting of the above-described reference value at an excessively large value may often result in splitting of a hair at the hair shaft or in a damage to a hair root so that papilla cells (see at reference sign a in FIG. 1) may remain on the side of the skin, thereby leading to a potential problem that the extraction of a biosubstance from the hair root may not be achieved well.

The present invention also provides a hair sampling device for the selective collection of a hair that has pulling force of a predetermined reference value to pull it out.

With reference to drawings, a description will hereinafter be made about certain preferred embodiments of the hair sampling device according to the present invention. It is to be noted that the embodiments to be described hereinafter illustrate certain representative embodiments of the present invention by way of example and the scope of the present invention shall not be narrowly interpreted by then.

Figure 3A:
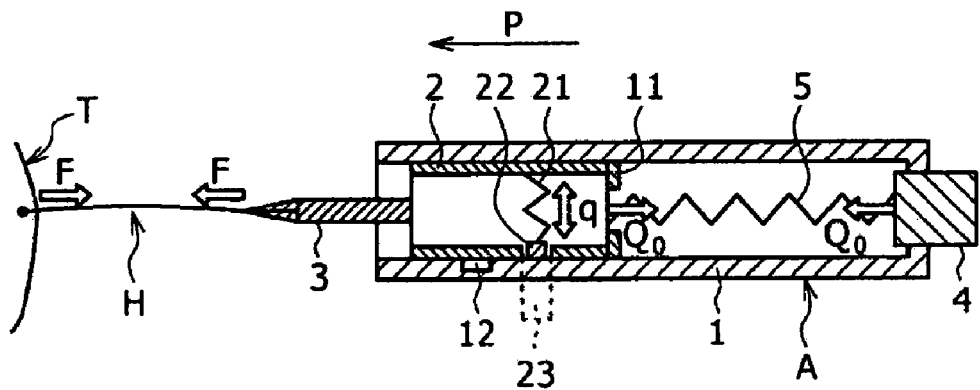
FIGS. 3A, 3B and 3C are cross-sectional views showing a hair sampling device according to a first embodiment of the present invention in different operation stages.
Figure 3B:
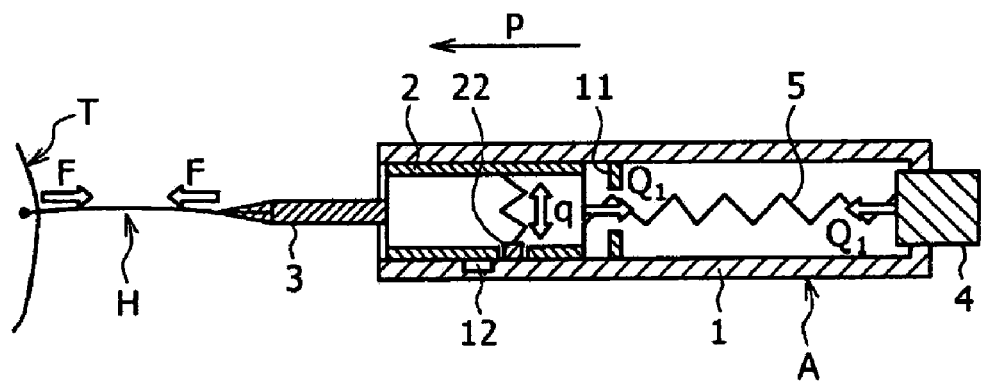
Figure 3C:
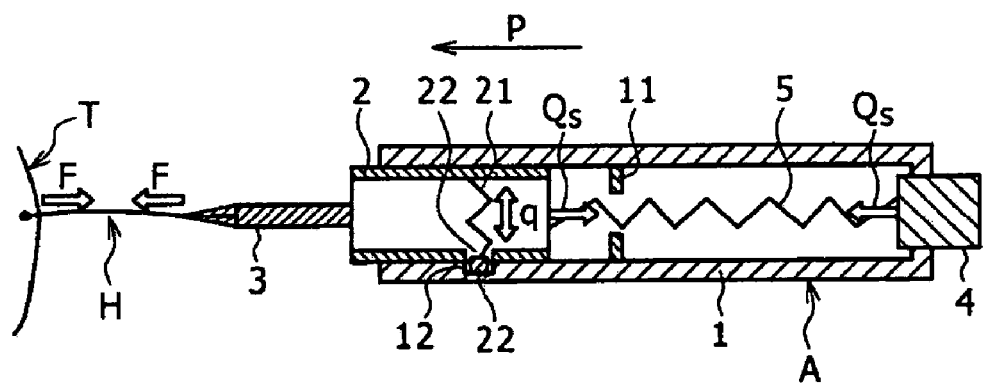

FIGS. 3A to 3C are cross-sectional views showing a hair sampling device according to a first embodiment of the present invention in different operation stages.

In FIG. 3A, the hair sampling device shown at reference sign A is equipped with an outer cylinder 1, an inner cylinder 2 movable in the direction of arrow P inside the outer cylinder, and a chuck assembly 3 as a section configured to hold a hair. The hair sampling device A holds at the chuck assembly 3 the hair designated at reference sign H, and pulls it out from the body surface T. To facilitate work in the course of the below-described extraction of a biosubstance in an easy manner, the chuck assembly 3 can preferably be designed to be detachably connected to the inner cylinder 2 by using a strong magnet or the like. In this figure, the outer cylinder 1, inner cylinder 2 and chuck assembly 3 are illustrated as metal-made members. However, their materials are not limited to metal, and as an alternative, they can be made of resin. It is to be noted that no particular limitation is imposed on the material of each member in the present invention unless otherwise specifically indicated.

Upon holding the hair H by the chuck assembly 3, it is desired to hold the hair H at a position within 10 mm from the body surface. This makes it possible to prevent the hair H from splitting at the hair shaft or to prevent damaging the hair root.

The hair sampling device A is also equipped with an outer-cylinder spring 5 as a section configured to measure pulling force applied to the chuck assembly 3 upon pulling out the hair H. The outer-cylinder spring 5 connects the inner cylinder 2 to a spring-force adjusting screw 4 located at an opposite end of the outer cylinder 1, and produces restoring force indicated by arrow $Q_0$. The outer cylinder 1 is provided with an inner-cylinder stopper plate 11, so that in an initial state, the inner cylinder 2 is held on the inner-cylinder stopper plate 11 by the restoring force $Q_0$. It is to be noted that in place of a spring, the outer-cylinder spring 5 can adopt one of a wide variety of resilient members capable of producing the restoring force $Q_0$. This applies equally to an inner-cylinder spring 21 to be described subsequently herein.

When the hair H is pulled by the hair sampling device A, pulling force F is applied to the chuck assembly 3 and inner cylinder 2.

When the pulling force F is smaller than the restoring force $Q_0$ applied to the inner tube 2 by the outer-cylinder spring 5, that is, $F<Q_0$, the chuck assembly 3 and inner cylinder 2 remain in the above-mentioned initial state (in the state held on the inner-cylinder stopper plate 11).

In other words, when the hair H is in a state to be readily pulled out and the pulling force F necessary for pulling out the hair H is smaller than the restoring force $Q_0$ ($F<Q_0$), the hair H is pulled out while the chuck assembly 3 and inner cylinder 2 remain in the above-mentioned initial state (in the state held on the inner-cylinder stopper plate 11).

When the hair H is in a state to be hardly pulled out and the pulling force F exceeds the restoring force $Q_0$, that is, $F>Q_0$, on the other hand, the chuck assembly 3 and inner cylinder 2 are pulled by the pulling force F and move in the direction of arrow P. As a result of the movement of the chuck assembly 3 and inner cylinder 2 at this time, the outer-cylinder spring 5 stretches so that the restoring force increases from the initial $Q_0$ to $Q_1$ ($Q_1>Q_0$) (see FIG. 3B).

It is to be noted that a stopper 22 connected to an inner wall of the inner cylinder 2 by the inner-cylinder spring 21 is disposed in the inner cylinder 2. By restoring force q produced by the inner-cylinder spring 21, the stopper 22 is pressed against the outer cylinder 1 through a stopper window 23 opening through a wall of the inner cylinder 2. In addition, a recessed portion 12 in which the stopper 22 can fit is arranged on an inner wall of the outer cylinder 1.

When the chuck assembly 2 and inner cylinder 2 move in the direction of arrow P by the pulling force F as depicted in FIG. 3C, the stopper 22 is brought into fitting engagement with the recessed portion 12 under a pressure by the restoring force q so that the inner cylinder 2 and chuck assembly 3 are restricted (locked) from moving in the direction of arrow P.

Now, assuming that the restoring force of the outer-cylinder spring 5 which competes with the pulling force F applied to the inner cylinder 2 and chuck assembly 3 at this time is $Q_s$, it can be considered that based on the restoring forces ($Q_0$, $Q_1$, $Q_s$), the outer-cylinder spring 5 exhibits the function of measuring the pulling force F in a range of from a lower limit $Q_0$ to an upper limit $Q_s$.

When the inner cylinder 2 and chuck assembly 3 are once locked as illustrated in FIG. 3C, the chuck assembly 3 overcomes the competition with the restoring force $Q_s$ and produces pulling force F as much as needed to pull out the hair H.

In other words, when pulling force F greater than the restoring force $Q_s$ is required to pull out the hair H, the chuck assembly 3 and the inner cylinder 2 are locked by the stopper 22 and then, the hair H is pulled out. When the hair H is pulled out under pulling force F not greater than the restoring force $Q_s$, on the other hand, the chuck assembly 3 and inner cylinder 2 return to the initial state (the state held on the inner-cylinder stopper plate 11) by the restoring force $Q_1$ without being locked.

As has been described above, the hair sampling device A can choose, while using as an indication the lock by the stopper 22, only the hair H that had pulling force F equal to or greater than a predetermined reference value (=the restoring force $Q_s$) to pull it out. It is to be noted that the restoring force $Q_s$ can be increased or decreased by the spring-force adjusting screw 4 and can be suitably changed depending on the position or the like of the hair H to be pulled out.

Figure 4:
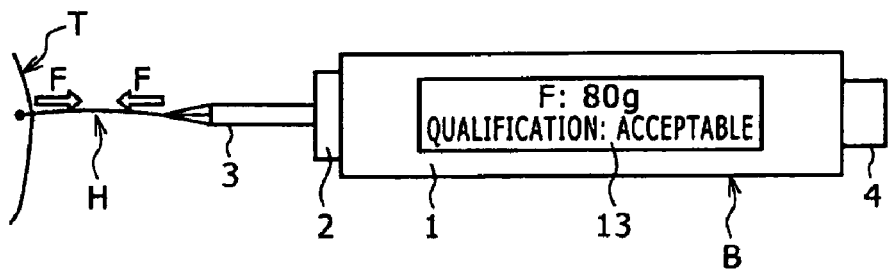
FIG. 4 is a front view showing a hair sampling device according to a second embodiment of the present invention.

FIG. 4 is a front view showing a hair sampling device according to a second embodiment of the present invention.

The hair sampling device designated at reference sign B in FIG. 4 is equipped inside an outer cylinder 1 with an unillustrated force sensor unit as a section configured to measure pulling force applied to a chuck assembly 3 upon pulling out a hair H and is also equipped on a surface of the outer cylinder 1 with a display unit 13. When the hair sampling device B is pulled with the hair H held on the chuck assembly 3, pulling force F applied to the chuck assembly 3 is measured by the force sensor unit and the pulling force F is digitally displayed at the display unit 13.

As already described, a hair which had pulling force of the predetermined reference value or greater to pull it out can be considered as a hair in the anagen phase (I) (see FIG. 1). The selection of such a hair has made it possible to obtain a biosubstance stably in both quantity and quality. The present inventors, however, found that, if a hair is puled out by excessively large pulling force far greater than the predetermined reference value, the hair is split at its hair shaft or its hair root is damaged to leave hair matrix cells (see the reference sign b in FIG. 1) on the side of the skin and the extraction of the biosubstance from hair root becomes poor. It is, therefore, desired to set an upper limit in addition to the lower limit with respect to the reference value for pulling force.

In this respect, the hair sampling device B digitally displays the pulling force F necessary for pulling out the hair H, and therefore, makes it possible to confirm whether or not the pulling force F falls between the lower limit and the upper limit. When the pulling force F necessary for pulling out the hair H falls between the predetermined lower limit and upper limit, "ACCEPTABLE" may also be displayed as a qualification result at the display 13 to further facilitate the confirmation. With the hair sampling device B, it is therefore possible to more easily select a hair suitable for the extraction of a biosubstance.

Figure 5A:
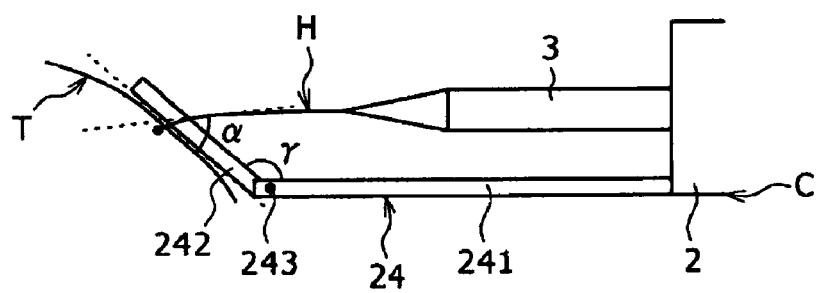
FIG. 5A is an enlarged front view showing a chuck assembly in a hair sampling device according to a third embodiment of the present invention.
Figure 5B:
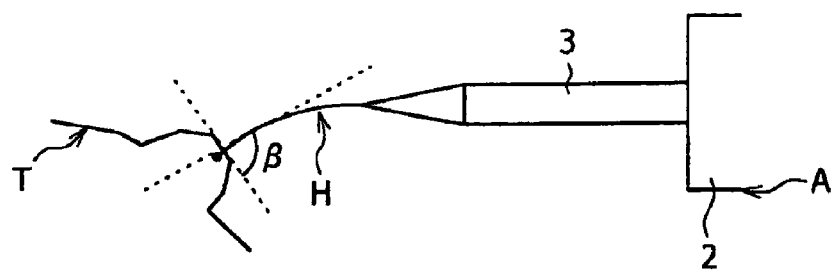
FIG. 5B is an enlarged front view of a chuck assembly in the hair sampling device of FIGS. 3A to 3C.
Figure 5C:
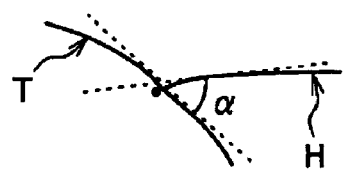
FIG. 5C is a diagram illustrating an angle of a growing direction of a hair relative to a body surface.

FIG. 5A is an enlarged front view of a chuck assembly 3 in a hair sampling device according to a third embodiment of the present invention. For the sake of comparison, an enlarged front view of the chuck assembly 3 in the hair sampling device A is shown in FIG. 53. In addition, FIG. 5C is a diagram for illustrating an angle of a growing direction of a hair H relative to a body surface T.

The hair sampling device indicated at reference sign C in FIG. 5A is equipped with an arm 24 as a section configured to specify the angle of the pull-out direction of the hair H relative to the body surface T. In this figure, the arm 24 is arranged in continuation with an inner cylinder 2. The arm 24 may, however, be arranged in continuation with an outer cylinder (not shown) or another member without being limited to the arrangement illustrated in the figure, and therefore, no particular limitation is imposed on the arrangement of the arm 24.

To extract a biosubstance stably from a hair root, it is necessary, in addition to the selection of a hair in the anagen phase (see FIG. 1), to avoid any damage to the hair root due to excessively large pulling force as mentioned above. The present inventors also found that the root of a hair may be damaged depending on the pull-out direction of the hair, and also revealed that it is effective for the prevention of such a damage to pull out a hair without changing the direction of the growing direction of the hair relative to the body surface.

Namely, the hair sampling device C makes it possible to pull out the hair H without changing the direction of the growing direction of the hair H relative to the body surface.

Described more specifically, now assume that in FIG. 5C, the hair H grows in the direction of an angle α relative to the body surface T. If the hair H is pulled out by the hair sampling device A not equipped with the arm 24, a part of the body surface H is pulled together with the hair H so that the angle α of the hair H relative to the body surface T changes from α to β.

In the case of the hair sampling device C, on the other hand, the arm 24 presses the body surface T so that the hair H can be pulled out while the initial angle α to the body surface T is maintained without pulling the body surface T.

Further, it is desired to adjust an angle γ between a support portion 241 and a body-surface contacting portion 242 suitably depending on the positions of the hair H and body surface T by constructing the arm 24 such that the support portion 241 and the body-surface contacting portion 242 are arranged in continuation with each other via a hinge pin 243. This construction further facilitates to pull out the hair H while maintaining the initial angle α to the body surface T.

Figure 6A:
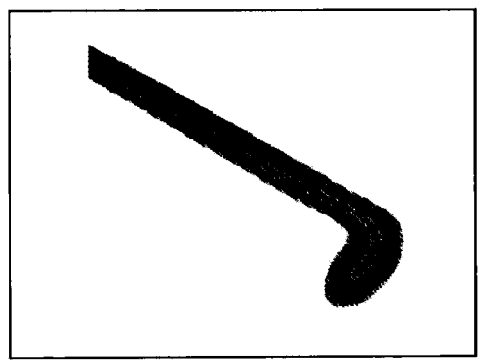
FIG. 6A shows an enlarged image of the root of a hair pulled out with the hair sampling device of FIGS. 3A, 3B and 3C.
Figure 6B:
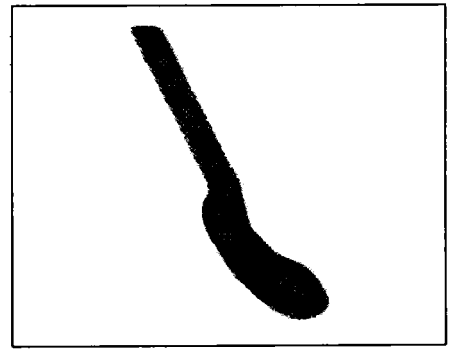
FIG. 6B shows an enlarged image of the root of a hair pulled out with the hair sampling device of FIG. 5A.

FIG. 6A shows an enlarged image of the root of a hair pulled out with the hair sampling device A of FIGS. 3A, 3B and 3C, and FIG. 68 shows an enlarged image of the root of a hair pulled out with the hair sampling device C of FIG. 5A. The end portion (hair bulb) of the hair root is greater in FIG. 68 than in FIG. 6A. The hair bulb of the hair root in FIG. 6B can, therefore, be estimated to contain a number of cells (hair matrix cells (see reference sign b in FIG. 1). In Examples, a description will be made about the results of extraction of a biosubstance from such hair roots.

Figure 7:
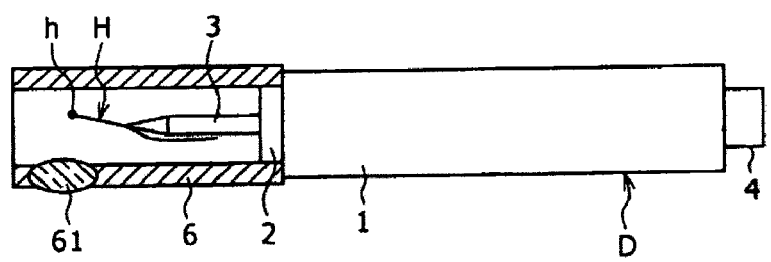
FIG. 7 is a front view of a hair sampling device according to a fourth embodiment of the present invention.

FIG. 7 is a front view of a hair sampling device according to a fourth embodiment of the present invention.

In FIG. 7, the hair sampling device designated at reference sign D is equipped with a magnifier 6 as a section configured to enable magnifying observation of the shape of the root of a pulled-out hair. With the hair sampling device D, the root h of a hair H held on the chuck assembly 3 after the hair H was pulled out can be magnified and observed by a lens 61 arranged in the magnifier 6. It is, therefore, possible to ascertain the shape of the pulled-out hair root h by visual observation as illustrated in FIG. 6.

Although the magnifier 6 is arranged as a section configured to enable magnifying observation of the shape of the root h of the hair H in the hair sampling device D, a microscope or the like can be arranged in place of the magnifier 6. A hair which permits good extraction of a biosubstance can be more simply and conveniently chosen by acquiring image information of a hair root with the microscope or the like, automatically determining the shape of the hair root in accordance with a computer program, and notifying its results to a laboratory technician.

Figure 8:
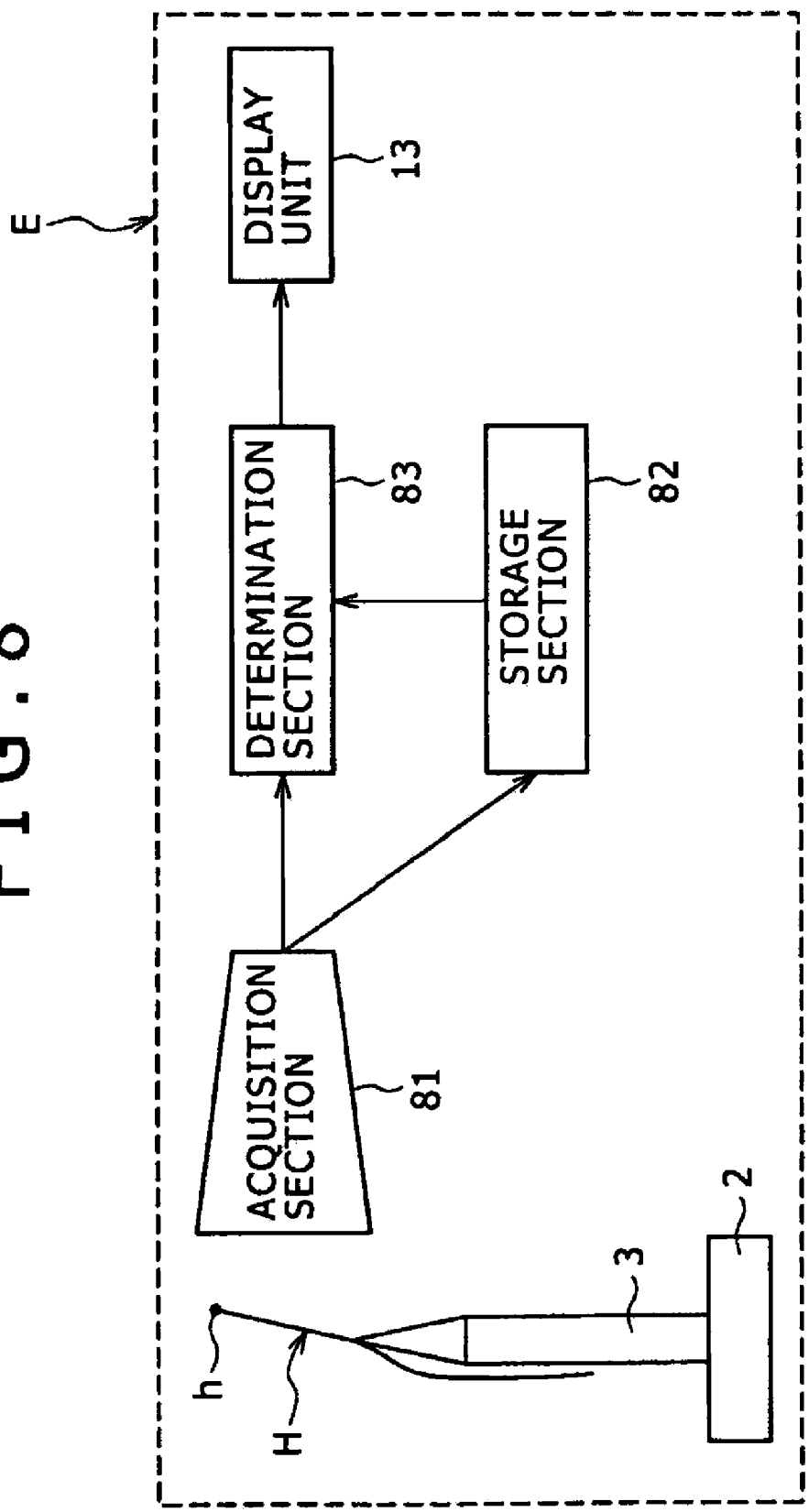
FIG. 8 is a concept diagram of a hair sampling device according to a fifth embodiment of the present invention.

FIG. 8 is a concept diagram illustrating a hair sampling device according to a fifth embodiment of the present invention.

In FIG. 8, the hair sampling device designated at reference sign E is equipped with an acquisition section 81 configured to acquire hair-root image information of a hair root h, a storage section 82 configured to store reference hair-root image information acquired beforehand, and a determination section 83 configured to determine the shape of the hair root h on the basis of the acquired hair-root image information.

The hair-root image information acquired by the acquisition section 81 is outputted to the determination section 83. As the acquisition section 81, a commonly-employed image pick-up device such as a CCD camera can be adopted.

Stored in the storage section 82 is hair-root image information (reference hair-root image information) on a hair root from which good extraction results were obtained as a result of the performance of extraction of a biosubstance subsequent to the advance acquisition of hair-root image information by the acquisition section 81. The stored reference hair-root image information is outputted to the determination section 83.

The determination section 83 determines the shape of the hair root h on the basis of a comparison of the hair-root image information inputted from the acquisition section 81 with the reference hair-root image information inputted from the storage section 82, and outputs the results of the determination to a display unit 13 (also see FIG. 4). Although the storage section 82 and determination section 83 can be constructed as discrete units as illustrated in the figure, they may be constructed as an integral unit by using a general-purpose computer.

The comparison between the hair-root image information of the hair root h and the reference hair-root image information by the determination section 83 can be performed using a general-purpose image analysis program or a program prepared by improving the first-mentioned program. It may be contemplated, for example, to perform the comparison by detecting inflection points on the contour of the hair root h and counting the inflection points on the basis of the hair-root image information or to perform the comparison by calculating the brightness of the hair root h.

Referring to FIG. 9 through FIG. 11B, a description will hereinafter be made about the method that determines the shape of the hair root h by detecting the inflection points on the contour of the hair root h and counting them.

Figure 9:
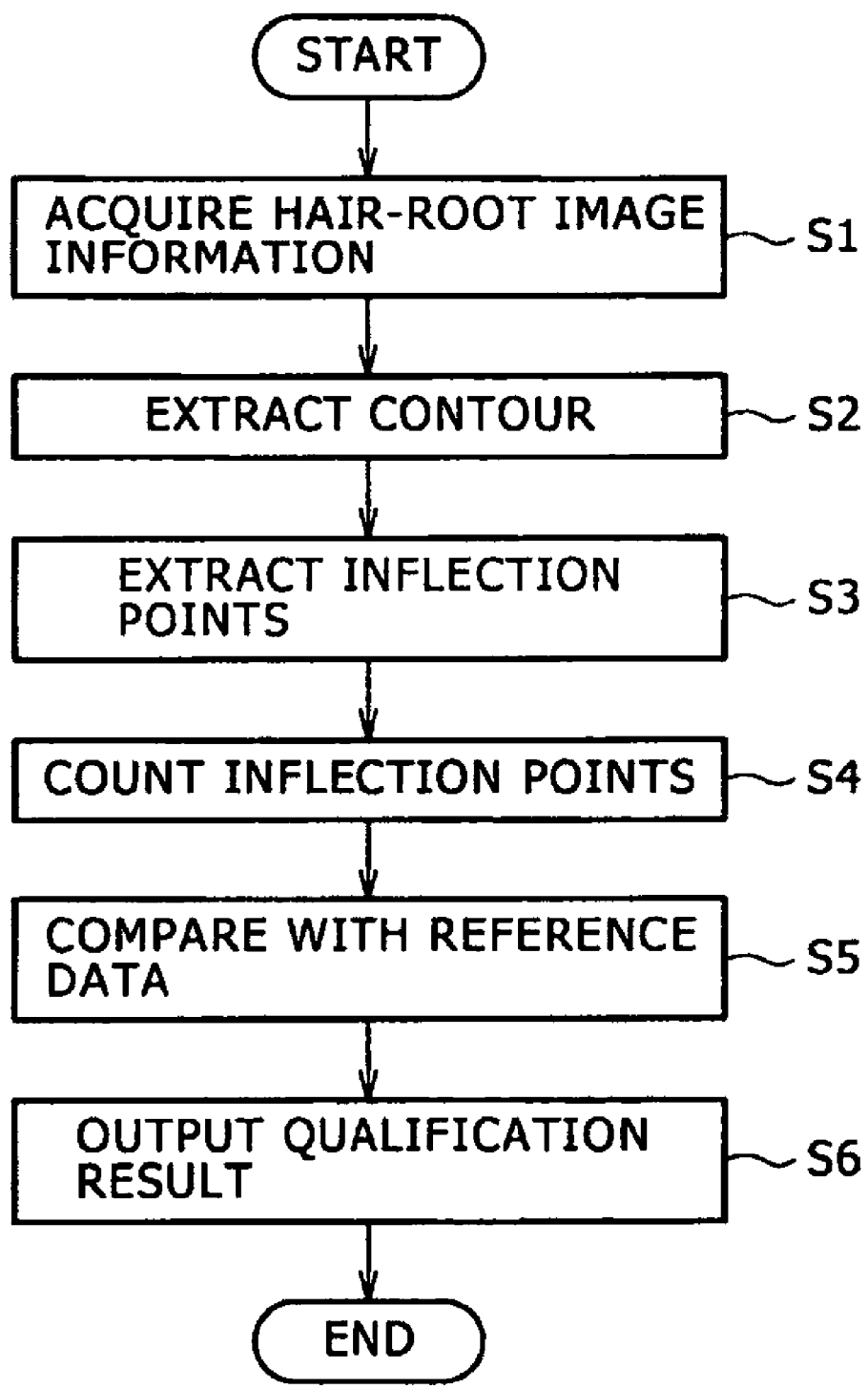
FIG. 9 is a flow chart illustrating a determination procedure at a determination section in the hair sampling device of FIG. 8.

FIG. 9 is a flow chart illustrating a determination procedure at the determination section 83 of FIG. 8.

In step 1 (which is indicated by "S1" in the figure; this will apply equally hereinafter), the determination section 83 firstly acquires hair-root image information of the hair root h from the acquisition section 81. In step S2, extraction of the contour of the hair root h is then performed based on the hair-root image information of the hair root h, followed by the extraction of inflection points on the contour in step S3 and the counting of the infection points in step S4.

The term "inflection point" as used herein means a boundary at which a concavity or convexity of a given function changes, in other words, a point at which the positiveness/negativeness of a gradient of the first differential function of the given function is reversed. In the present invention, the term "inflection point", therefore, means a boundary at which a concavity or convexity of the contour of the hair root h changes, that is, a point at which the positiveness/negativeness of the gradient of a tangential line to the contour is reversed.

Figure 10A:
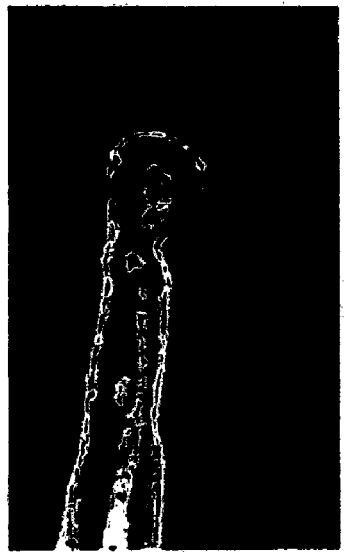
FIG. 10A shows an image of a hair root as acquired in step S1 of FIG. 9 by an acquisition section in the hair sampling device of FIG. 8.
Figure 10B:
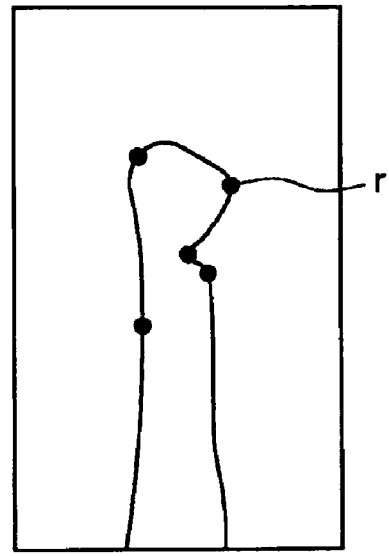
FIG. 10B depicts a contour of the hair root and inflection points thereof as extracted from the hair root image of FIG. 10A.
Figure 11A:
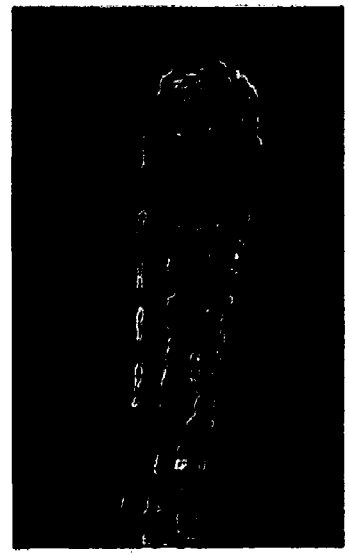
FIG. 11A shows an image of another hair root as acquired in step S1 of FIG. 9 by an acquisition section in the hair sampling device of FIG. 8.
Figure 11B:
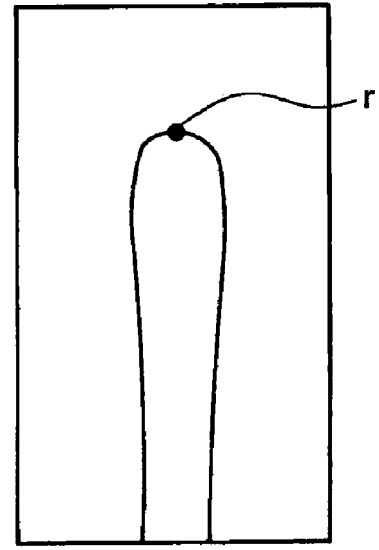
FIG. 11B depicts a contour of the hair root and inflection points thereof as extracted from the hair root image of FIG. 11A.

FIGS. 10A through 11B illustrate specific examples of the contours of hair roots and their inflection points as extracted in steps S2 and S3. FIGS. 10A and 11A show hair-root images acquired by the acquisition section 81, while FIGS. 10B and 11B depict the contours and inflection points of the hair roots as extracted from the hair-root images. The number of inflection points designated at reference sign r is five in FIG. 10B and one in FIG. 11B.

Subsequently, the determination section 83 compares the number of inflections as calculated in step S5 with a reference number of inflection points as calculated from the reference hair-root image information in a similar manner to determine the shape of the hair root h, and outputs the results of the determination to the display unit 13 (step S6).

The reference number of inflection points can be set as desired depending on the quantity and quality of a desired biosubstance. As will be described subsequently in the Examples, the present inventors have already found that the extraction of a good biosubstance is feasible when the number of inflection points of a hair root is large and the contour of the hair root defines a complex shape. When the number of inflection points of the hair root h is greater than the reference number of inflection points, the determination section 83, therefore, outputs the results of a determination to the effect that "the hair is suited for the extraction of the biosubstance," and at the display unit 13, a display is made accordingly. When the number of inflection points of the hair root h is conversely smaller than the reference number of inflection points, the determination section 83 outputs the results of a determination to the effect that "the hair is not suited for the extraction of the biosubstance," and at the display unit 13, a display is made accordingly.

As an alternative, it may be contemplated to conduct the determination of the shape of the hair root h at the determination section 83 by calculating the brightness of the hair root h in the hair-root image.

The term "brightness" as used herein means a difference in lightness in an image of a hair root, specifically the ratio of the lightness of a region captured lightest to that of a region captured darkest (light region/dark region), and it means that the greater this light/dark ratio, "the higher the brightness". Alternatively, this light/dark ratio can also be defined as the high density/low density ratio (low-density region/high-density region) in the image of the hair root, and can be considered to be synonymous with the magnitude of a difference in density between the density of a region captured darkest and the density of a region captured lightest.

As will be described subsequently in the Examples, the present inventors have already found that the good extraction of a biosubstance is feasible when the brightness is high. Based on this finding, it is possible to determine the shape of the hair root h by calculating the brightness on the basis of hair-root image information and comparing it with the reference brightness calculated from the reference hair-root image information, both at the determination section 83.

As has been described above, the hair sampling device E makes it possible to more properly select a hair suited for the extraction of a biosubstance by automatically determining the shape of a hair root and displaying the results of the determination.

Based on FIGS. 12A through 12F, a description will next be made about a specific method for the extraction of a biosubstance from a pulled-out hair.

As a kit for the convenient and sure extraction of a biosubstance from a pulled-out hair, the present inventors have contrived an extraction kit depicted in FIGS. 12A through 12F. As problems associated with the extraction of a biosubstance from a hair, there are damages to the hair root and quality deteriorations of the biosubstance due to contamination in the course of the extraction work because of the difficulties in handling the hair after its collection or sampling. For these problems, analysis results became unstable in certain instances even when appropriate hairs were collected or sampled by such methods as described above. The present invention, therefore, provides an extraction kit, which can be easily handling by a laboratory technician and can surely receive therein the root of a collected or sampled hair.

A description will hereinafter be made specifically about how to use the extraction kit. A hair H held on the chuck assembly 3 of one of the hair sampling devices A to D is removed integrally with the chuck assembly 3 from an unillustrated inner cylinder (see FIG. 12A). It was mentioned above to the effect that the chuck assembly 3 may preferably be designed detachably with the inner cylinder 2 by using a strong magnet or the like to facilitate the work in the extraction procedure. Needless to say, it is also possible to conduct the work without detaching the chuck assembly 3.

The hair H held on the chuck assembly 3 is then inserted into a slit 72 formed in a cap 71 in such a manner that the hair H is pushed toward the center of the cap 71 (see FIG. 12B). By this operation, each pulled-out hair H can be surely provided for extraction work. It is to be noted that in FIG. 12B, ($B_1$) indicates a side view of the cap 71 as viewed from the side of the slit 72 and ($B_2$) designates a top view of the cap 71.

A main body 73 depicted in FIG. 12C is equipped with a cover 74, and is internally filled with an extraction solvent 75. When the cap 71 is progressively fitted into the main body 73 together with the hair H held in the slit 71 in the preceding step, the slit 72 is closed so that the cap 71 more firmly holds the hair H and seals the extraction solvent 75 at the same time. At this time, the root h of the hair H is immersed in the extraction solvent 75 (see FIG. 12D).

As illustrated in FIG. 12E, the cover 74 is then closed over the cap 71 to completely seal the cap 71 and extraction solvent 75 within the main body 73, and subsequently, the main body 73 is turned upside down such that the cover 74 becomes the bottom side (see FIG. 12F).

The bottom wall of the main body 73 is provided with a pipette inserting portion 76 which can be pierced by the free end of a pipette tip t. The extraction kit is, therefore, constructed such that by using the pipette, the extraction solvent 75 can be stirred and drawn up and another reagent can be injected.

As a consequence, it is possible to complete the extraction work of the biosubstance from the hair h within the main body 73. For example, the incorporation of a resin, silica beads or the like, which can adsorb nucleic acids thereon, in the extraction solvent 75 makes it possible to adsorb on the resin, silica beads or the like nucleic acids dissolved out from the hair root h in the extraction solvent 75. The extraction of the nucleic acids is then conducted by pipetting, specifically drawing up the extraction solvent and injecting a washing solution or a re-dissolving solvent.

As will be described subsequently, investigations were conducted about effects of the method of the present invention for the extraction of a biosubstance. Among biosubstances such as RNA, DNA, proteins and elements, RNA is particularly prone to degradation so that its handling is difficult. The provision of good RNA in a large quantity is, therefore, an important factor that affects the reproducibility of an experiment. In the Examples, the investigations were hence conducted by specifically taking RNA as a target biosubstance.

Example 1

Investigations on Pulling Force

In this Example, an investigation was conducted with human hairs to determine relationships between the pulling forces necessary to pull out the hairs and the quantities and qualities of extracted RNA.

The hairs were pulled out from an area on the back of the head at a position between both of the ears, specifically at an interaural center (median) part. From the root of the pulled-out hair, a solution of total RNA (hereinafter simply called "RNA") was prepared by an RNA extraction kit ("RNEASY MICRO KIT", tradename; product of Qiagen) in accordance with the furnished protocol (see RNeasy micro.pdf, pages 11 to 16). Using "AGILENT RNA 600 NANO KIT" (tradename, product of Agilent Technologies), the concentration of RNA was measured by "BIOANALYZER 2100" (tradename, manufactured by Agilent Technologies). The protocol furnished by the manufacture was followed (see RNA6000 nano.pdf).

Figure 13:
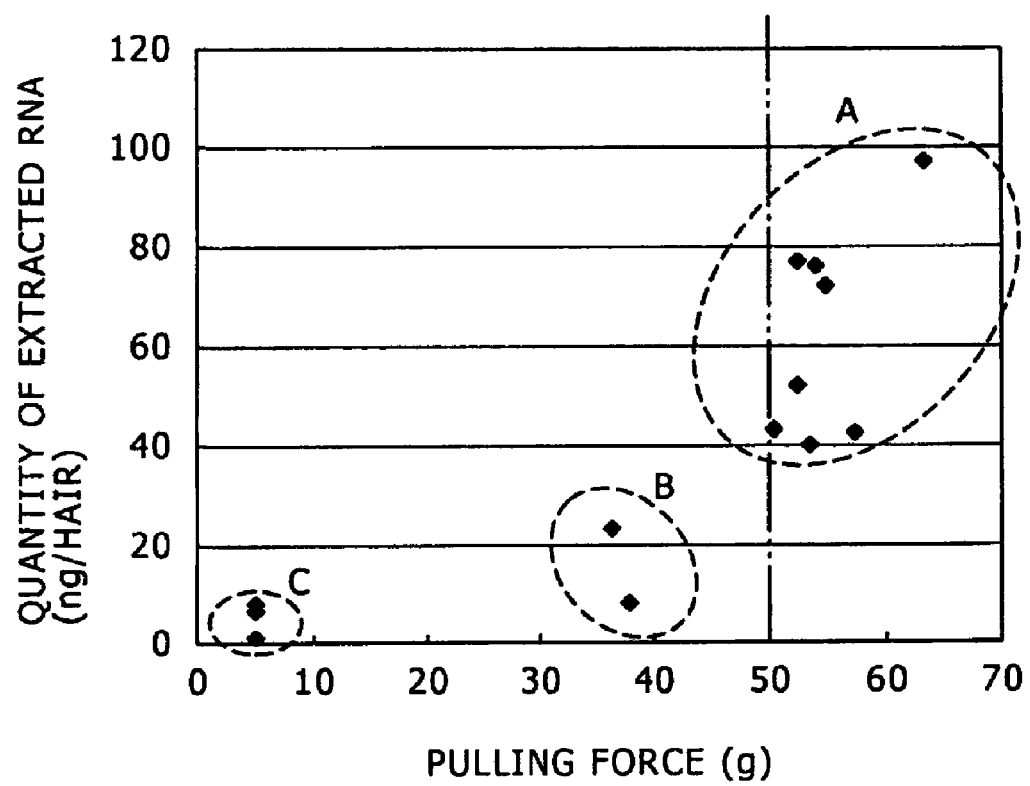
FIG. 13 is a diagram illustrating a relationship between pulling force necessary for pulling out a hair and a quantity of extracted RNA.

The results are shown in FIG. 13, in which the abscissa represents the puling force (g) necessary to pull out each hair and the ordinate represents the concentration (ng/hair) of an RNA solution extracted from the hair.

With hairs had pulling force as high as 50 g or greater (Group A in the figure), high-concentration RNA solutions of 40 ng/hair or higher were extracted. With both of hairs had pulling force of from 35 to 40 g (Group B) and hairs had pulling force as low as 5 g (Group C), on the other hand, the concentrations of the resulting RNA solutions were as low as 25 ng/hair or lower. It is to be noted that for Group C, those fallen off when hair was finger-combed were used by taking them as hairs pulled out with pulling force of 5 g.

From the foregoing, it has been indicated that a high-concentration RNA solution can be stably prepared by using pulling force of 50 g as a reference value and extracting RNA from the root of a hair which has pulling force of the reference value or greater.

An investigation was next conducted as to the qualities of RNAs extracted from the hairs in Group A to Group C.

As already mentioned, RNA has the property that it is very unstable and is prone to degradation. In degraded RNA, the messenger RNA (mRNA) is also cut. Upon conducting the synthesis of cDNA from the mRNA by reverse transcriptase, a problem arises in that cDNA may not be synthesized or only short-fragment cDNA can be synthesized. In this case, a gene expression analysis making use of the cDNA can hardly be performed either.

As a method for confirming the quality of RNA, it has been the practice to isolate RNA by electrophoresis and then to confirm the bands of ribosomal RNA (18sRNA and 26sRNA) in the past. With RNA the degradation of which has proceeded, the bands of the ribosomal RNA decrease or disappear. With undegraded RNA of good quality, on the other hand, the bands of ribosomal RNA can be clearly confirmed.

Using "RNA 6000 NANOKIT" (tradename, product Agilent Technologies), the RNA solutions extracted from the hairs in Group A to Group C were each electrophoretically isolated and the intensities of the bands of ribosomal RNA (18sRNA and 26sRNA) were measured, both, by "BIOANALYZER 2100" (trade name, manufactured by Agilent Technologies). The protocol furnished by the manufacture was followed (see RNA6000 nano.pdf).

Figure 14A:
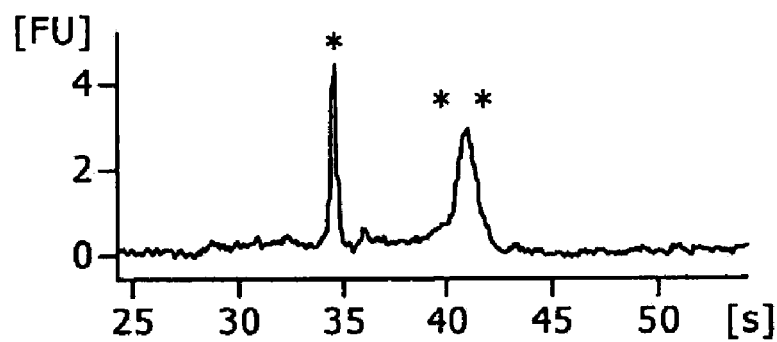
FIGS. 14A to 14C diagrammatically illustrate electrophoresis patterns of RNAs extracted from groups of hairs which had different levels of pulling force upon pulling them out, respectively.
Figure 14B:
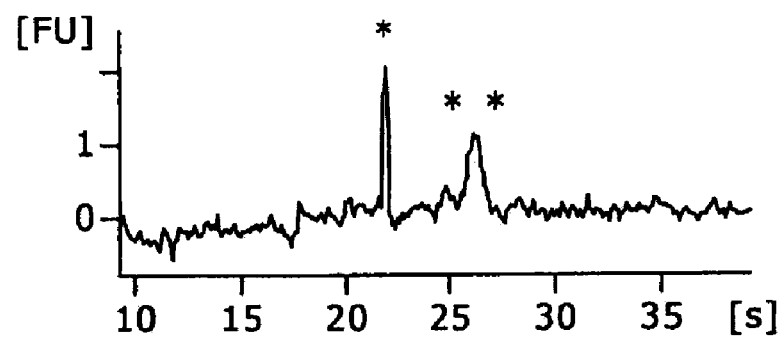
Figure 14C:
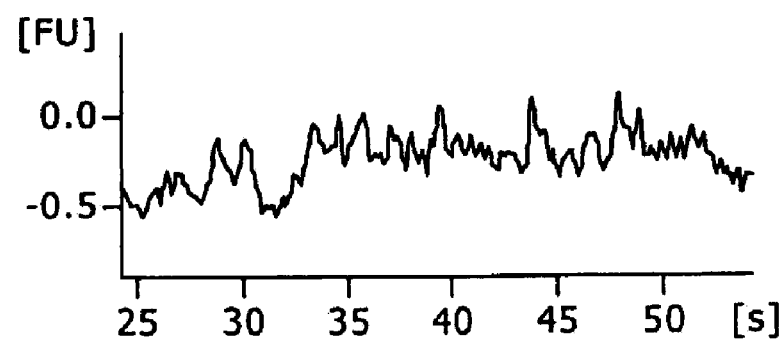

The results are shown in FIGS. 14A to 14C, in each of which the abscissa represents electrophoresis time (second(s)) and the ordinate represents band intensity (fluorescence unit (FU)).

FIG. 14A shows an electrophoresis pattern of the RNA extracted from Group A (one of the hairs which had pulling force of 50 g or greater) in FIG. 13. Around an electrophoresis time of 35 s, a band ascribable to 18sRNA (see * in the figure) was detected at a high intensity of 4 FU or more. Similarly, around an electrophoresis time of 40 s, a band ascribable to 26sRNA (see ** in the figure) is observed at high intensity.

With the RNA extracted from Group B (one of the hairs which had pulling force of from 35 to 40 g) in FIG. 13, on the other hand, bands ascribable to 18sRNA and 26sRAN, respectively, are observed as peaks, but their fluorescence intensities are pronouncedly lower compared with those of the bands for Group A, specifically as low as around 2 FU in the case of the band ascribable to 18sRNA (see FIG. 14B; note the scale in the direction of the ordinate). This indicates that the degradation of RNA proceeded more in Group B than in Group A.

Turning to the RNA extracted from Group C (one of the hairs which had pulling force of 5 g) in FIG. 13, bands ascribable to 18sRNA and 26sRNA were not observed, and the electrophoresis failed to detect any fluorescence itself which was ascribable to RNA (see FIG. 14C).

From the foregoing, it has been indicated that a high-quality RNA solution can be stably prepared by using pulling force of 50 g as a reference value and extracting RNA from the root of a hair which has pulling force of the reference value or greater.

Using the RNAs extracted from Group A (the hairs which had pulling force of 50 g or greater) in FIG. 13, an investigation was next conducted about the reproducibility of the results of a gene expression analysis.

As a control group, hairs pulled out at random from a similar site as Group A were used. RNAs were extracted by the above-described method from the hairs of Group A and the control group, cDNA synthesis was conducted using reverse transcriptase by a method known in the related art, and the expression levels of GAPDH gene were measured. GAPDH gene is known as a so-called "housekeeping" gene, and is employed as an indication of a gene expression level in a gene expression analysis.

Figure 15:
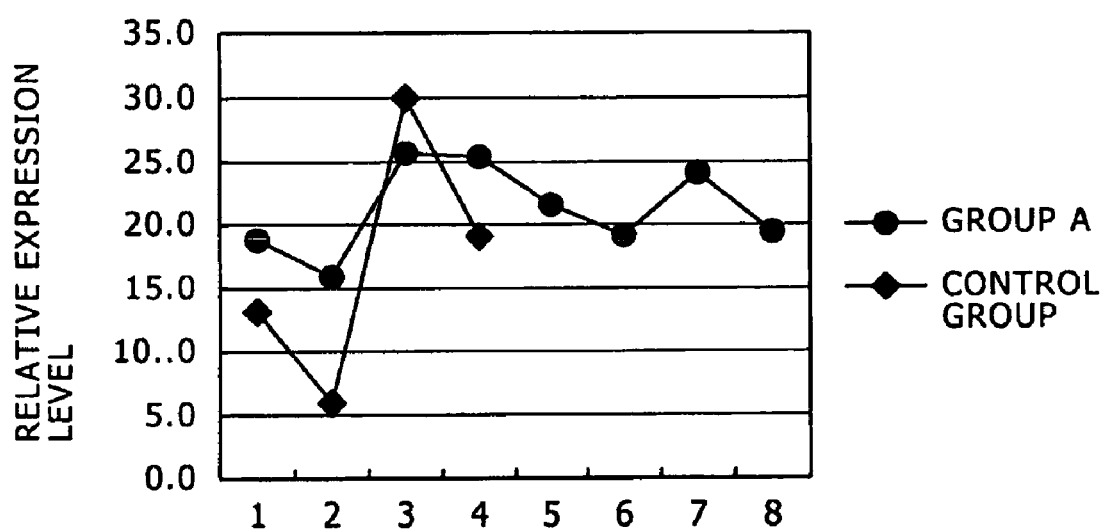
FIG. 15 is a diagram showing the results of gene expression analyses of the GAPDH gene obtained using RNA extracted from hairs in Group A of FIG. 13 and those in a control group, respectively.

The results are shown in FIG. 15, in which the abscissa represents the sample numbers of the hairs in Group A and the control group and the ordinate represents the relative expression levels of GAPHD gene in the respective samples.

It is appreciated that compared with the control group indicated by filled rhombuses, the expression levels of GAPDH gene in Group A as indicated by filled circles in the figure are smaller in the difference between the maximum value and the minimum value and have smaller variations. Accordingly, the expression level of GAPDH gene was successfully quantitated with high reproducibility among the respective samples in Group A.

From the foregoing, it has become evident that a high-reproducibility gene expression analysis is feasible by using pulling force of 50 g as a reference value and extracting RNA from the roots of hairs which have pulling force of the reference value or greater.

Example 2

Investigations on Pull-Out Direction and Hair-Root Shape

In this example, investigations were conducted as to relationships between the angle of the pull-out direction of a hair relative to the body surface and the shape of the pulled-out hair root and the quantity and quality of the extracted RNA.

FIG. 16A shows an enlarged image of the root of a hair pulled out without allowing the angle of its growing direction to change relative to the body surface by using a section configured to specify the angle of the pull-out direction of the hair to the body surface, FIG. 16B depicts an enlarged image of the root of a hair pulled out at a non-specified angle, and FIG. 16C is a table presenting concentrations of RNA solutions extracted from those hair roots, respectively.

The end portion (hair bulb) in the hair root is greater in FIG. 16B than in FIG. 16A. It is, therefore, possible to estimate that many cells (hair matrix cells (see reference sign b in FIG. 1)) are contained in the hair root shown in FIG. 16B.

Concerning the quantities of RNA extracted from those hair roots, the quantity of RNA extracted from the hair pulled out at the specified angle as shown in FIG. 16B was 93.93 ng/hair, and therefore, was significantly greater compared with 40.14 ng/hair as the quantity of RNA extracted from the hair pulled out at the non-specified angle as shown in FIG. 16A.

From the foregoing, it has been indicated that the quantity of RNA to be extracted from the root of a hair is increased by pulling out the hair with a section that specifies the angle of the pull-out direction of the hair relative to the body surface.

Figure 17A:
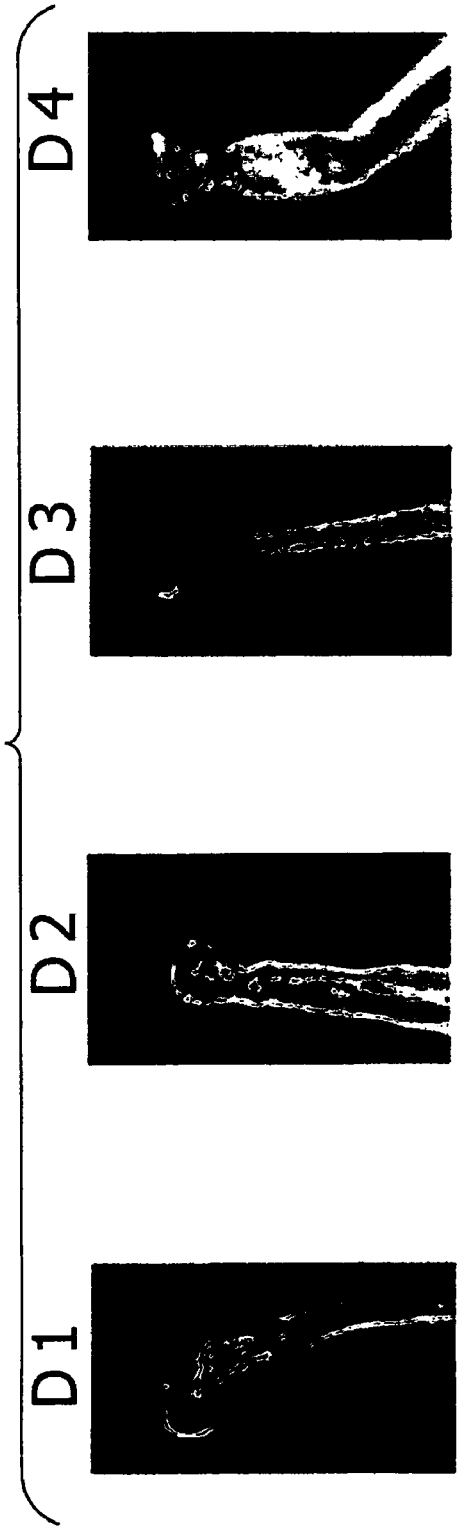
FIG. 17A (D1 through D4) show images of hair roots the contours of which each had three or more inflection points, and FIG. 17B (E1 through E4) depict images of hair roots the contours of which each had two or fewer inflection points.
Figure 17B:
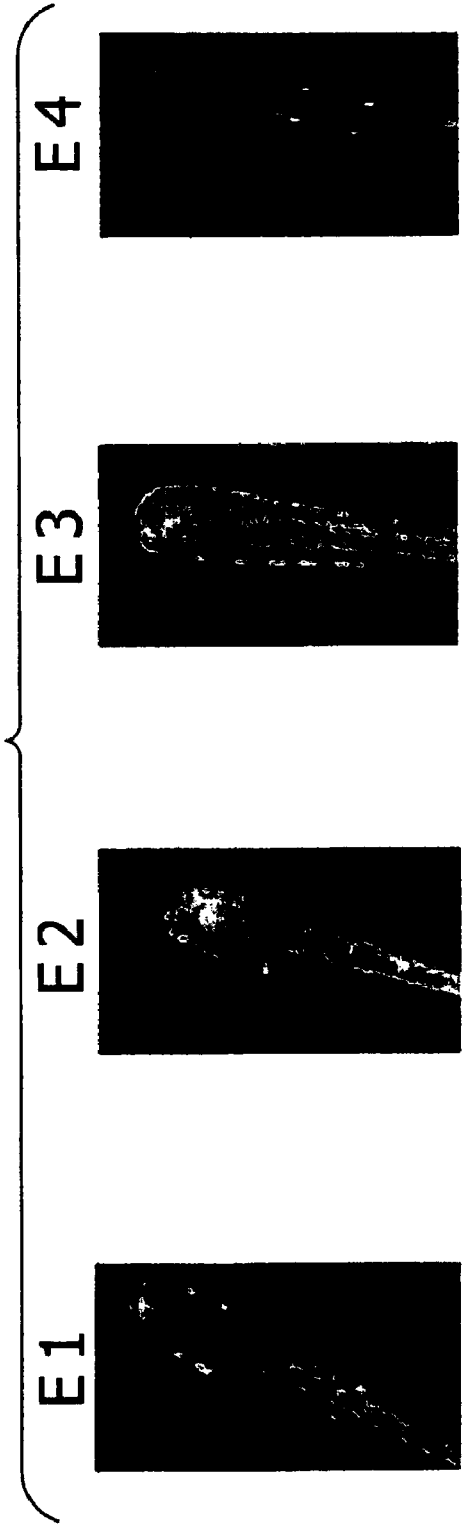

FIG. 17A (D1 through D4) show images of the hair roots of pulled-out hairs, the contours of which each had three or more inflection points (Group D); and FIG. 17B (E1 through E4) depict images of the hair roots of pulled-out hairs, the contours of which each had two or fewer inflection points (Group E). It is to be noted that the hair shown in E4 was cut at the hair shaft thereof when pulled out.

Table 1 presents the quantities and qualities of RNAs extracted from the hair roots in Group D and Group E. Each RNA quantity is presented in terms of the concentration (pg/μL) of a corresponding RNA solution prepared by the procedure described in Example 1. It is to be noted that the extraction of RNA was not feasible from the hair shown in E4.

Each RNA quality is indicated by the ratio of existing ribosomal RNA (26sRNA/18sRNA) as obtained by conducting the electrophoresis of RNA and the measurement of band intensities in a similar manner as in Example 1, FIGS. 18A and 18B (D1 through E4) illustrate electrophoresis patterns of the respective samples. The greater the 26sRNA/18sRNA, the better the quality of RNA. It is to be noted that with respect to Group E, the extracted quantities of RNA were too little to evaluate their qualities.

TABLE 1

| Sample | RNA quantity (pg/μL) | RNA quality (26s/18s) |
|---|---|---|
| D1 | 551 | 2.0 |
| D2 | 368 | 1.5 |
| D3 | 513 | 1.7 |
| D4 | 302 | 1.7 |
| E1 | 47 | — |
| E2 | 55 | — |
| E3 | 9 | — |
| E4 | — | — |

As presented in Table 1, it has been confirmed that the RNAs extracted from the hair roots in Group D, the hair roots each having three or more inflection points, were excellent in both quantity and quality compared with the RNAs extracted from the hair roots in Group E, the hair roots each having two or fewer inflection points. This indicates that a hair root having a greater number of inflection points on its counter and having a more complex shape makes it possible to extract a better biosubstance.

As appreciated from FIGS. 17A and 17B (D1 through E4), the hair roots in Group D were higher in brightness (light/dark ratio or high/low density ratio) than the hair roots in Group E. It is, therefore, suggested that a hair root of higher brightness makes it possible to extract a better biosubstance.

The biosubstance extraction method according to the present embodiment can be used in various analyses such as gene expression analyses, gene polymorphism analyses and proteome analyses, all of which use micro-volume samples, and can contribute to the elucidation of the mechanisms of diseases, the search for drug targets, and the like. The hair sampling device according to the present embodiment, on the other hand, facilitates the collection or sampling of hairs at clinical sites, and therefore, contributes to the accumulation of analysis data and the establishment of diagnosis methods based on the analysis data.

It should be understood by those skilled in the art that various modifications, combinations, sub-combinations and alterations may occur depending on design requirements and other factors insofar as they are within the scope of the appended claims or the equivalents thereof.

What is claimed is:

1. A hair sampling device for pulling out a hair, comprising:
   means for holding said pulled-out hair;
   means for measuring pulling force applied to said hair when said hair is pulled out;
   means for acquiring hair-root image information on said pulled-out hair;
   means for storing reference hair-root image information; and
   means for determining a shape of a root of said pulled-out hair based on a comparison between the hair-root image information and the reference hair-root image information, wherein the comparison is performed by detecting inflection points on a contour of said pulled-out hair and counting said inflection points.

2. The hair sampling device according to claim 1, further comprising:
   means for specifying a pull-out direction of said pulled-out hair relative to a body surface.

3. The hair sampling device according to claim 1, further comprising:
   means for enabling magnifying observation of a shape of a root of said pulled-out hair.

4. A hair sampling device for pulling out a hair, comprising:
   a section configured to hold said pulled-out hair;
   a storage device storing a program; and
   a processor executing the program to:
      acquire hair-root image information corresponding to said pulled-out hair;
      acquire reference hair-root image information;
      detecting inflection points on a contour of said pulled-out hair;
      counting said inflection points;
      comparing the hair-root image information and the reference hair-root image information by using the counted inflection points; and
      determine a shape of a root of said pulled-out hair based on a result of the comparison.

5. The hair sampling device according to claim 4, further comprising:
   a section for specifying a pull-out direction of said pulled-out hair relative to a body surface.

6. The hair sampling device according to claim 4, further comprising:
   a magnifier for enabling magnifying observation of a shape of the root of said pulled-out hair.

7. The hair sampling device according to claim 4, wherein the processor determines, based on the determined shape, whether the pulled-out hair is a suitable specimen for extracting a biosubstance from the hair-root.

8. The hair sampling device according to claim 4, wherein comparing the hair-root image information and the reference hair-root includes comparing the counted number of inflection points with a reference value included in the reference hair-root image information.

9. The hair sampling device according to claim 4, wherein the reference hair-root image information is stored in the storage device.

10. The hair sampling device according to claim 4, wherein the processor executes the program to calculate a brightness of the root based on the hair-root image information.

11. The hair sampling device according to claim 10, wherein determining a shape of the root of said pulled-out hair includes comparing the calculated brightness with a reference brightness calculated from the reference hair-root image information.

12. The hair sampling device according to claim 1, further comprising means for determining, based on the determined shape, whether the pulled-out hair is a suitable specimen for extracting a biosubstance from the hair-root.

13. The hair sampling device according to claim 1, wherein comparing the hair-root image information and the reference hair-root includes comparing the counted number of inflection points with a reference value included in the reference hair-root image information.

14. The hair sampling device according to claim 1, further comprising means for calculating a brightness of the root based on the hair-root image information.

15. The hair sampling device according to claim 14, wherein determining a shape of the root of said pulled-out hair includes comparing the calculated brightness with a reference brightness calculated from the reference hair-root image information.

16. A hair sampling device for pulling out a hair, comprising:
- means for holding said pulled-out hair;
- means acquiring hair-root image information corresponding to the root of the pulled-out hair;
- means for detecting inflection points on a contour of the hair-root by using the hair-root image information;
- means for counting a number of inflection points;
- means for determining a shape of the root of the pulled-out hair based on the number of inflection points; and
- means for determining, based on the determined shape, whether the pulled-out hair is a suitable specimen for extracting a biosubstance from the hair-root.

17. The hair sampling device according to claim 16, wherein the shape of the root is determined based on a comparison between the number of inflection points and a reference value included in reference hair-root image information.

18. The hair sampling device according to claim 17, wherein the pulled out hair is determined to be a suitable specimen when the number of inflection points is greater than the reference value.

19. The hair sampling device according to claim 16, further comprising means for displaying an indication when the pulled-out hair is determined to be a suitable specimen.

* * * * *